United States Patent [19]

Pesa et al.

[11] Patent Number: 4,469,886

[45] Date of Patent: Sep. 4, 1984

[54] SELECTIVE HYDROCARBOXYLATION OF PROPYLENE TO ISOBUTYRIC ACID

[75] Inventors: Frederick A. Pesa, Aurora; Thomas A. Haase, University Heights, both of Ohio

[73] Assignee: The Standard Oil Company, Cleveland, Ohio

[21] Appl. No.: 368,533

[22] Filed: Apr. 15, 1982

Related U.S. Application Data

[63] Continuation-in-part of Ser. No. 206,817, Nov. 14, 1980, abandoned.

[51] Int. Cl.$^3$ .................... C07C 51/14; C07C 53/124
[52] U.S. Cl. ...................................... 562/522; 562/599
[58] Field of Search ......................... 562/522; 260/413

[56] References Cited

U.S. PATENT DOCUMENTS

| | | | |
|---|---|---|---|
| 3,168,553 | 2/1965 | Slaugh | 560/232 |
| 3,437,676 | 4/1969 | Kutepow et al. | 560/232 |
| 3,501,513 | 3/1970 | Kutepow et al. | 560/232 |
| 3,641,074 | 2/1972 | Fenton | 260/410.9 R |
| 3,661,949 | 5/1972 | Fenton | 260/413 |
| 3,816,490 | 6/1974 | Forster et al. | 260/413 |
| 3,839,378 | 10/1974 | Yamoguchi et al. | 260/413 |
| 3,855,307 | 12/1974 | Rony et al. | 560/232 |
| 3,856,856 | 12/1974 | Nozaki | 562/519 |
| 3,857,900 | 12/1974 | Wilkinson | 252/431 R |
| 3,859,319 | 1/1975 | Mrowca | 260/410.6 |
| 3,887,595 | 6/1975 | Nozaki | 260/410.6 |
| 3,919,272 | 11/1975 | Knifton | 260/410.9 R |
| 3,933,919 | 1/1976 | Wilkinson | 252/431 R |
| 3,968,133 | 7/1976 | Knifton | 260/410.9 R |

Primary Examiner—Vivian Garner
Attorney, Agent, or Firm—Thomas P. Schur; Joseph G. Curatolo; Larry W. Evans

[57] ABSTRACT

A process for the selective hydrocarboxylation of propylene to produce predominantly isobutyric acid in the liquid phase is provided. The reaction of propylene, carbon monoxide and water is effected at a temperature of about 75° C. to about 150° C. and at a pressure of about 250 psi to about 5000 psi in the presence of a suitable solvent and a catalyst comprising palladium or a palladium compound, a phosphoamine promoter ligand compound and a hydrogen halide.

20 Claims, No Drawings

SELECTIVE HYDROCARBOXYLATION OF PROPYLENE TO ISOBUTYRIC ACID

This application is a continuation in part of U.S. Pat. No. 206,817, filed Nov. 14, 1980, abandoned.

BACKGROUND OF THE INVENTION

This invention relates to the hydrocarboxylation of olefins to form carboxylic acids. More specifically, this invention relates to the hydrocarboxylation of propylene with CO and $H_2O$ in the liquid phase to produce butyric acid, wherein the branched or "iso" butyric acid isomer product predominates. The isobutyric acid may then be dehydrogenated to produce methacrylic acid.

Conventionally, hydrocarboxylation of olefins has been intended to produce predominantly the linear, straight-chain or normal (n) isomer of the carboxylic acid desired.

U.S. Pat. No. 3,641,074 to Fenton discloses the preparation of normal or straight chained carboxylic acids, esters and anhydrides via the carbonylation of olefins in the presence of a Group VIII noble metal in complex association with a biphyllic ligand. Suitable ligands may include triarylphosphine and triarylarsine among others.

U.S. Pat. No. 3,816,490 to Forster et al. discloses the production of carboxylic acids by carboxylation of olefins, utilizing a Group VIII metal compound, preferably cobalt, rhodium and iridium together with a phenolic promoter compound. The metal compound may be elemental metal, a simple salt, or an organometallic complex such as a phosphine. The reaction yields predominantly normal carboxylic acids when isomeric products are to be prepared.

U.S. Pat. No. 3,856,856 to Nozaki discloses the carbonylation of alcohols using platinum-promoted cobalt/iodide in catalysts which may be promoted by phosphine ligands including triphenylphosphine and substituted triphenylphosphines such as tris (4-dimethylaminophenyl) phosphine.

U.S. Pat. Nos. 3,857,900 and 3,933,919 to Wilkinson disclose hydrogenation, hydroformylation and carbonylation reactions resulting primarily in the formation of linear products when catalysts comprising platinum group metals, ligands containing nitrogen, phosphorus, arsenic or antimony; and a halogen or pseudo-halogen are utilized.

U.S. Pat. No. 3,859,319 to Mrowca discloses carboalkoxylation of unsaturates using a catalyst comprising an organophosphorus palladium halide containing bridging phosphido groups and optionally including a tin salt promoter. The catalyst includes organophosphorus ligands such as di(lower alkyl)amino phosphines. The linear product predominates using such a catalyst system, usually over 80% linear.

U.S. Pat. No. 3,887,595 to Nozaki discloses the carbonylation of olefinic compounds to yield a high ratio of straight chain to branch-chain products using catalysts comprising a zero valent palladium or platinum complex, and a triorgano phosphine ligand, $R_3P$. The R groups may comprise dialkylamino hydrocarbyls and dialkyl aminophenyls. An acid halide is not present in the reaction.

U.S. Pat. Nos. 3,919,272 and 3,968,133 to Knifton disclose the preparation of linear fatty acids and esters from olefins, carbon monoxide and alcohols or water in the presence of ligand-stabilized palladium halide complexes in combination with a halide salt of either tin or germanium. Ligands may include phosphines, arsines and amines among others.

The preparation of increased ratios of branched-chain or iso-carboxylic acids to straight-chain acids is described in U.S. Pat. No. 3,661,949 to Fenton. Olefins are hydrocarboxylated in the presence of a biphyllic ligand-stabilized Group VIII noble metal compound catalyst and an iron halide co-catalyst. The ligand may include arsines or phosphines.

U.S. Pat. No. 3,437,676 to Kutepow et al. discloses the carbonylation of olefins using palladium salt catalysts which may be complexed with phosphine ligands among others. Exemplified are mixed ligand systems, such as in example 82 in which the palladium dichloride catalyst is complexed with benzylamine and with triphenylphosphine. The iso/n ratio of the products described in Kutepow '676 is generally less than 2.5 to 1.

U.S. Pat. No. 3,501,518 to Kutepow et al. discloses the preparation of carboxylic acids or esters from olefins utilizing a supported or nonsupported catalyst comprising metallic palladium or a palladium chalcogenide, an acid and an organic phosphine or nitrile.

U.S. Pat. No. 3,855,307 to Rony et al. discloses multiphase catalysts comprised of a porous solid carrier upon which a liquid-phase catalyst is disposed. The catalyst may comprise metals complexed with ligands including phosphines, arsines, amines, among others, and such catalysts may be useful for hydroformylation and carbonylation reactions. The exemplified reactions demonstrate that the products obtained are predominantly composed of normal-chain hydrocarbons.

In general, the single metal salt catalyst systems are non-selective for the "iso" form of the carboxylic acid products, tending to yield either predominantly straight chain products, or a slightly favored distribution of iso-products. Any catalyst system to be utilized in the hydrocarboxylation reaction must be thermally stable at the temperatures required for the reaction to effectively occur. Other factors which effect the hydrocarboxylation reaction are the molar ratios of catalyst to stabilizing ligands, to the reactants, and to other components of the system.

SUMMARY OF THE INVENTION

It is therefore an object of the present invention to provide a process for the hydrocarboxylation of propylene in the liquid phase, to produce butyric acid.

It is a further object of the present invention to provide a process for the hydrocarboxylation of propylene in the liquid phase to produce predominantly the isobutyric acid isomer product.

It is a further object of the present invention to provide a process for the hydrocarboxylation of propylene in the liquid phase to produce isobutyric acid utilizing an active palladium catalyst system which is thermally stable, and which does not readily lose selectivity at the reaction temperatures required.

These and other objects of the present invention, together with the advantages thereof, which shall become apparent from the specification that follows, are accomplished by the invention as hereinafter described and claimed.

In general, the process of the present invention includes the preparation of predominantly isobutyric acid in the liquid phase. A reaction mixture is formed from propylene, carbon monoxide and water in a suitable solvent in the presence of an active palladium catalyst system. The reaction mixture is subjected to a temperature of about 75° C. to about 150° C. and a pressure of about 250 psi to about 5000 psi. The catalyst system generally includes palladium or a palladium compound, a phosphoamine promoter ligand compound and a hydrogen halide.

DETAILED DESCRIPTION OF THE INVENTION

The preparation of the iso or branched isomer of butyric acid from propylene, carbon monoxide and water in the liquid phase proceeds according to the following catalyzed reaction.

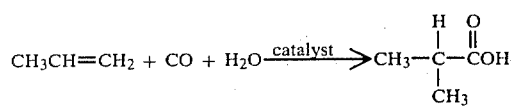

The formation of n-butyric acid, in which all the carbon atoms form a straight chain, is to be minimized to the greatest extent possible.

The production of predominantly the "iso" form of butyric acid is made possible by the choice of catalyst system, including stabilizing and promoting ligands and complexing acids. The following reaction mechanism has been proposed for the preparation of isobutyric acid from propylene, carbon monoxide and water. This mechanism is merely theoretical and in no way is intended to limit the scope of the present invention, but rather is provided to illustrate the subject reaction.

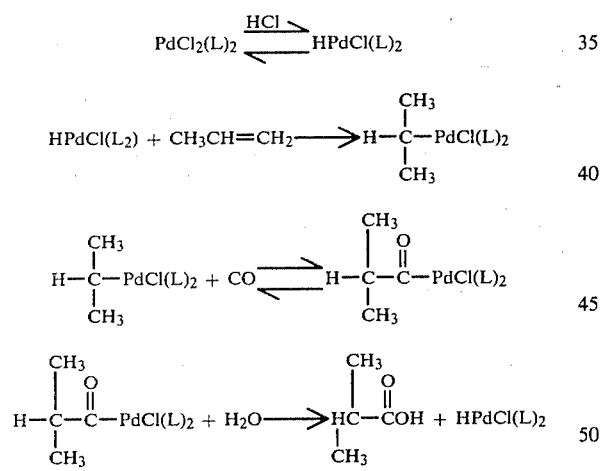

The catalyst system according to the present invention includes a phosphoamine ligand stabilized promoted, palladium or a palladium compound together with a complexing hydrogen halide acid, preferably hydrochloric acid, optionally with other strong acids, preferably in addition to HCl.

The palladium or palladium compound utilized according to the present invention is capable of coordinating carbon monoxide, propylene and water as is demonstrated in the reaction mechanism above. It is preferred that the palladium component of the catalyst be present as a solution of a palladium salt in at least the +2 valence state. Suitable palladium salts include palladium acetate, palladium chloride, palladium nitrate and the like. The molar ratio of propylene fed in the reaction to the palladium present, whether in a batch-type reaction or a continuous reaction, is about 1:1 to about 1000:1, preferably about 100:1.

The catalyst system, that is, the palladium or palladium compound and its ligand promoter, may be easily recovered after reaction by separating the products from the reaction mixture by conventional methods, such as distillation.

The transformation of the palladium catalyst which is selective to the production of isobutyric acid to a non-selective form is inhibited in part by the incorporation of stabilizing ligands in the catalyst system. Stabilizing ligands which function effectively as promoters to the subject reaction include phosphoamines of the general formula

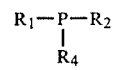

wherein at least one of $R_1$, $R_2$ and $R_4$ is an amino group represented by the formula

and $R_1$, $R_2$, $R_4$, $R_5$ and $R_6$ are defined as follows. $R_1$, $R_2$ and $R_4$ are independently selected from the above amino group, alkyls having from 1 to about 12 carbon atoms, aryls, meta- or para-positioned substituent-containing aryls and substituent-containing alkyls having from about 1 to about 12 carbon atoms. $R_5$ and $R_6$ are independently selected from hydrogen, alkyls having from 1 to about 12 carbon atoms, aryl, meta- or para-positioned substituent-containing aryls, and substituent-containing alkyls having from 1 to about 12 carbon atoms.

The substituents $R_1$, $R_2$, $R_4$, $R_5$ and $R_6$ may therefore be selected from the following:

(1) $C_1$ to $C_{12}$ alkyls;
(2) $-O(CH_2)_a CH_3$, where $a = 0$ to about 11;
(3)

$$-(CH_2)_b \underset{\underset{OH}{|}}{C}=O,$$

where $b = 0$ to about 11;
(4)

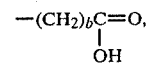

where $d = 0$ to about 10; $e = 0$ to about 10 and $d + e \leq 10$;
(5)

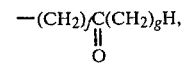

where $f = 0$ to about 11, $g = 0$ to about 11; and $f + g \leq 11$;
(6)

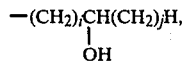

where i=0 to about 11, j=0 to about 11; and i+j≦11;

(7) —(CH$_2$)$_k$X, where X=F, Cl, Br or I and k=1 to about 12;

(8) —(CH$_2$)$_m$CN, where m=0 to about 11; and (9)

where Y is meta or para positioned and is selected from groups 1 through 8 above, and z=0 to 2. R$_5$ and R$_6$ may also include H. The substituents must not adversely affect the hydrocarboxylation reaction under the conditions of the process, and must be stable at the reaction conditions used. We have found that phosphines in which a hydrocarbon group such as a phenyl group separates phosphorus from an amine group, (P is not bonded to N) such as tris-4 dimethylaminophenyl phosphine, are not stable under reaction conditions, tending to decompose over the course of the reaction.

Triaminophosphines, particularly tris-dimethylaminophosphine, are preferred stabilizing/promoting ligands. Other phosphoamine stabilizing ligands include, but are not limited to, tris (N,N-diphenyl) amino phosphine; tris (N,N-ditolyl) amino phosphine; triaminophosphine; N,N-dimethylamino dimethyl phosphine; N,N-diphenylamino methylphenyl phosphine; N,N-dioctylamino methyl orthotolylphosphine; N,N-dimethylamino (methoxy methyl) methyl phosphine; tris (N,N-diethyl) amino phosphine and the like.

Phosphoamines may be prepared according to methods known in the art. For example, PCl$_3$ or chloro-substituted phosphines such as dichlorophenyl phosphine may be combined with ammonia or a secondary amine, mixed and heated to form the ligands. The molar ratio of PR$_3$/Pd according to the present invention is within the range of about 1:1 to about 100:1, and preferably is in the range of about 2:1 to 50:1.

The catalyst system requires a hydrogen halide which is capable of being coordinated with the palladium metal ion. Hydrogen chloride is preferred and may be supplied to the reaction in aqueous or anhydrous form or as a compound which is capable of releasing HCl under the reaction conditions. HBr and HI can also be used, but the activity of the catalyst system is lower when these are used alone. Mixtures of HCl and HBr or HCl and HI are also used to lend stability to the system. Other strong acids may be added to the system as a complexing acid in addition to the hydrogen halide, such as H$_2$S, H$_2$SO$_4$, HCN, H$_3$PO$_4$ and HBF$_4$. The amine may also be protonated.

The halide component of the hydrogen halide should be present in a molar ratio of about 5:1 to about 500:1 with respect to the palladium in the system. A preferred ratio of HCl/Pd is from about 50:1 to about 150:1, throughout which range conversion and selectivity to isobutyric acid remain high. The HCl/Pd ratio of 90:1 is most preferred. The molar ratio of propylene fed in the reaction to the halide component present is preferably within the range of about 1:1 to about 1000:1.

Suitable solvents according to the present invention include inert organic solvents such as benzene or substituted aromatic compounds, carboxylic acids such as acetic acid, esters, ethers such as dioxane, aldehydes, ketones and the like. The product acid may also be utilized as the solvent.

The reaction of the propylene, carbon monoxide and water in the presence of the ligand-stabilized palladium catalyst should be conducted at a temperature in the range of about 75° C. to about 150° C. Preferred temperatures are within the range of about 90° C. to about 125° C. At low temprature, the rate of reaction is unacceptably slow, and at temperatures higher than about 150° C. the catalyst system becomes unstable.

The molar ratio of water to propylene in the reaction medium should be maintained with the range of about 0.01:1 to about 10:1. It is preferred that the molar ratio of water to propylene be maintained at about 0.5:1 to about 2:1.

The reaction should be carried out under a carbon monoxide pressure of about 250 psi to about 5000 psi. Preferred CO pressures are from about 400 psi to about 1200 psi. It has been found that maintaining the reaction at these pressures results in a favorable rate of reaction, and an increase of selectivity to isobutyric acid. Maintaining the reaction at high pressure additionally allows a greater throughput to desired products per unit of time.

SPECIFIC EMBODIMENTS OF THE INVENTION

A series of exempletive reactions were carried out in a 300 ml Hastelloy C autoclave in pyrex glass liners. Although the examples were carried out as a batch-type reactions to illustrate the present invention, it is intended that the scope of the present invention include continuous feed-type reactions also. Analysis of liquid product was performed on a Hewlett-Packard 5710 A gas chromatograph. Valeric acid was used as the internal standard, and column packing was Polyester FF (trademark of Nishio Industries). Analysis of gases was performed on a Carle III gas analyzer using a Houdry dual column with thermisters as detectors.

The reaction in the examples set forth below were run in the following manner. A pre-weighed amount of palladium acetate, promoter ligand, solvent, water and hydrogen halide was placed into the glass liner. The promoter ligands, and the concentrations of promoter ligands and hydrogen halide were varied as set forth in the examples and Table below.

After the addition of the above to the autoclave, the autoclave was sealed and mechanical stirring begun. The autoclave was flushed once with an 800 psi charge of carbon monoxide. The propylene was then added to the autoclave from a pre-weighed bomb and the amount of propylene added was measured by weight difference. Carbon monoxide was added to bring the pressure of the autoclave up to 450 psi. The temperature was then increased to the run temperature, and the time was recorded. Carbon monoxide was added to the reactor as needed after it reached run temperature and pressure by the use of a reservoir filled with carbon monoxide. A record of the rate of carbon monoxide addition was made using a pressure transducer attached to a recorder. After the reaction was completed, the autoclave was cooled with cold running water. The entire volume of gas vented from the autoclave was collected in a multi-layered gas sampling bag, measured using a wet test meter, and a sample was injected into the Carle III gas analyzer. The liquid effluent was weighed and analyzed as set forth above.

The results of the reaction runs are reported in the Table below as follows.

$$\% \text{ Conversion} = \frac{\text{Moles of all Products Produced} \times 100}{\text{Moles of Propylene Fed}}$$

TABLE

Hydrocarboxylation of Propylene Using Pd $(CH_3COO)_2$/P $[N(CH_3)_2]_3$/HCl Catalyst System

| Example | Catalyst Ratio[a] | Pressure PSI | Time (Min) | Grams Propylene | % Conv. | Selectivity % Isobutyric | % N Butyric | ISO/N Ratio |
|---|---|---|---|---|---|---|---|---|
| 1 | 1:2:90 | 450 | 60 | 15.38 | 47.2 | 79.5 | 20.5 | 3.87 |
| 2 | 1:20:90 | 450 | 75 | 27.24 | 83.9 | 78.7 | 21.3 | 3.69 |
| 3[b] | 1:20:90 | 850 | 90 | 27.45 | 74.8 | 71.1 | 16.8 | 4.23 |
| 4 | 1:48:90 | 850 | 60 | 27.80 | 14.7 | 73.3 | 18.8 | 3.89 |
| 5[c] | 1:20:150 | 800–900 | 75 | 26.21 | 62.4 | 70.9 | 16.5 | 4.29 |
| 6 | 1:51:138 | 800–900 | 90 | 27.36 | 28.9 | 64.4 | 15.7 | 4.11 |
| Comp. A | 1:2:90[d] | 450 | 120 | 14.23 | 52.4 | 67.2 | 32.8 | 2.04 |
| Comp. B | 1:2:90[d] | 450 | 60 | 14.33 | 67.8 | 71.4 | 28.6 | 2.49 |

[a] Catalyst ratio = molar ratio of Pd:PR$_3$:HCl
[b] Reaction Temperature 95° C.
[c] Solvent = octanoic acid
[d] Promoter ligand - triphenylphosphine $$\% \text{ Selectivity} = \frac{\text{Moles of Isobutyric Acid Produced} \times 100}{\text{Moles of All Products}}$$

EXAMPLES 1–6

In Examples 1–6 inclusive, 0.1185 g palladium acetate was added to about 100 ml solvent (acetic acid except for example 5 in which octanoic acid was used) together with an amount of tris-dimethylaminophosphine and HCl (38%) sufficient to establish the catalyst ratios set forth in the Table; about 9.08 g water was added in each example.

The catalysts prepared in Examples 1–6 were run according to the procedure set forth above. The results of the reaction runs together with the reaction pressure, amount of propylene fed and reaction time are reported in the Table. Unless noted differently in the Table, the reactions were run at a temperature of 110° C. and a carbon monoxide pressure of at least 450 psi in about 100 ml acetic acid solvent. The molar ratio of water to propylene in the reaction mixture was maintained in a ratio of about 0.5:1 to about 2:1.

COMPARATIVE EXAMPLES A & B

In comparative examples A & B, the procedures set forth above were repeated, except that the promoter ligand added was triphenylphosphine.

As can be seen from the above Examples and Table, the hydrocarboxylation of propylene with carbon monoxide and water in the presence of a catalyst comprising palladium or a palladium compound, a phosphoamine ligand compound and a hydrogen halide, produces a high conversion to butyric acid, particularly with an unexpectedly high selectivity to isobutyric acid, generally of about 70% or greater. The ratio of isobutyric acid to n-butyric acid produced by the process of the present invention is 3.5 or greater, compared to less than 2.5 which is achieved when promoter ligands such as triphenylphosphine, described in the prior art, are used.

Thus it should be apparent to those skilled in the art that the subject invention accomplishes the objects set forth above. It is to be understood that the subject invention is not to be limited by the examples set forth herein. These have been provided merely to demonstrate operability, and the selection of specific palladium salts, type of phosphoamine stabilizer/promoter ligand, hydrogen halide, solvents and reaction conditions can be determined from the total specification disclosure provided without departing from the spirit of the invention herein disclosed and described, the scope of the invention including modifications and variations that fall within the scope of the attached claims.

We claim:

1. A process for the selective hydrocarboxylation of propylene to produce butyric acid in the liquid phase at a temperature of about 75° C. to 150° C. and a pressure of about 250 psi to about 5000 psi, wherein the isobutyric acid isomer product predominates, comprising forming a reaction mixture of propylene, carbon monoxide and water in the presence of a catalyst comprising palladium or a palladium compound, a hydrogen halide and a phosphoamine ligand represented by the formula $$R_1-\underset{\underset{R_4}{|}}{P}-R_2$$

wherein at least one of $R_1$, $R_2$ and $R_4$ is an amino group represented by the formula $$\underset{\underset{R_5}{|}}{N}-R_6$$

wherein $R_1$, $R_2$ and $R_4$ are additionally, independently selected from, and $R_5$ and $R_6$ are independently selected from:

(1) $C_1$ to $C_{12}$ alkyls;
(2) $-O(CH_2)_aCH_3$, where $a = 0$ to about 11;
(3)

$$-(CH_2)_b\underset{\underset{OH}{|}}{C}=O,$$

where $b = 0$ to about 11;
(4)

$$-(CH_2)_d\underset{\underset{O}{\|}}{C}O(CH_2)_eCH_3,$$

where $d=0$ to about 10; $e=0$ to about 10 and $d+e \leq 10$;

(5)

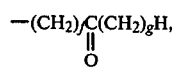

where $f=0$ to about 11, $g=0$ to about 11; and $f+g \leq 11$;

(6)

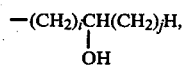

where $i=0$ to about 11, $j=0$ to about 11; and $i+j \leq 11$;

(7) $-(CH_2)_k X$, where $X=F$, Cl, Br or I and $k=1$ to about 12;

(8) $-(CH_2)_m CN$, where $m=0$ to about 11; and (9)

where Y is meta- or para-positioned and is selected from groups (1) through (8) above, and $z=0$ to 2; and wherein $R_5$ and $R_6$ are additionally, independently selected from hydrogen.

2. A process as recited in claim 1, wherein the reaction is carried out at a temperature of about 90° C. to about 125° C.

3. A process as recited in claim 1, wherein the pressure is maintained at about 400 psi to 1200 psi.

4. A process as recited in claims 1 or 3 wherein said pressure is exerted substantially by carbon monoxide.

5. A process as recited in claim 1 wherein said palladium compound is a palladium salt selected from the group consisting of palladium acetate, palladium chloride, and palladium nitrate.

6. A process as recited in claim 1, wherein $R_1$, $R_2$ and $R_4$ are each an amino group.

7. A process as recited in claim 1 wherein said phosphoamine is tris-dimethylaminophosphine.

8. A process as recited in claim 1 wherein said hydrogen halide is HCl.

9. A process as recited in claim 1 wherein a strong acid in addition to HCl is included in the reaction mixture.

10. A process as recited in claim 1 wherein said reaction mixture includes an inert organic solvent.

11. A process as recited in claim 10 wherein said inert organic solvent is selected from the group consisting of benzene, carboxylic acids, esters, ethers, aldehydes, ketones and mixtures thereof.

12. A process as recited in claim 11 wherein said solvent comprises a carboxylic acid.

13. A process as recited in claim 1 wherein the molar ratio of propylene to palladium is about 1:1 to about 1000:1.

14. A process as recited in claim 1 wherein the molar ratio of propylene to palladium is about 100:1.

15. A process as recited in claim 1 wherein the molar ratio of phosphoamine to palladium is about 1:1 to about 100:1.

16. A process as recited in claim 1 wherein the molar ratio of phosphoamine to palladium is about 2:1 to about 50:1.

17. A process as recited in claim 1 wherein the molar ratio of hydrogen halide to palladium is about 5:1 to about 500:1.

18. A process as recited in claim 1 wherein the molar ratio of hydrogen halide to palladium is about 50:1 to about 150:1.

19. A process as recited in claim 1 wherein the water to propylene ratio is about 0.01:1 to about 10:1.

20. A process as recited in claim 1 wherein the water to propylene ratio is about 0.5:1 to about 2:1.

* * * * *